United States Patent
Giordano

(10) Patent No.: US 7,682,835 B2
(45) Date of Patent: Mar. 23, 2010

(54) METHOD AND DEVICE OF RAPID ANTIGEN EXTRACTION

(75) Inventor: Paolo Giordano, Segrate (IT)

(73) Assignee: ABS Advanced Biomedical Systems S.r.l., Milan (IT)

(*) Notice: Subject to any disclaimer, the term of this patent is extended or adjusted under 35 U.S.C. 154(b) by 0 days.

(21) Appl. No.: 11/803,549

(22) Filed: May 15, 2007

(65) Prior Publication Data

US 2007/0286768 A1  Dec. 13, 2007

Related U.S. Application Data

(63) Continuation-in-part of application No. 11/312,167, filed on Dec. 20, 2005, now abandoned.

(51) Int. Cl.
*G01N 33/543* (2006.01)

(52) U.S. Cl. .................................................. 436/518

(58) Field of Classification Search ................ 435/7.9
See application file for complete search history.

(56) References Cited

U.S. PATENT DOCUMENTS

| | | | |
|---|---|---|---|
| 4,150,950 A | 4/1979 | Takeguchi et al. | |
| 4,673,639 A | 6/1987 | Slifkin et al. | |
| 4,851,337 A | 7/1989 | Berke et al. | |
| 5,415,994 A | 5/1995 | Imrich et al. | |
| 5,869,272 A | 2/1999 | Bogart et al. | |
| 6,180,395 B1 | 1/2001 | Skiffington et al. | |
| 6,660,469 B1 | 12/2003 | Wright et al. | |
| 7,455,195 B2 * | 11/2008 | Mekata ........................ | 222/94 |

FOREIGN PATENT DOCUMENTS

| | | |
|---|---|---|
| EP | 0 659 437 B1 | 12/1994 |
| JP | 7059555 | 3/1995 |
| WO | WO 95/25948 | 3/1995 |

OTHER PUBLICATIONS

Manual of Clinical Microbiology Fourth Edition, Streptococci and Aerococci, Richard R. Facklam and Roberta B. Carey, Chapter 16, pp. 154-175, American Society for Microbiology, Washington, D.C. 1985.

* cited by examiner

*Primary Examiner*—Ann Y Lam
(74) *Attorney, Agent, or Firm*—Dilworth & Barrese, LLP.

(57) ABSTRACT

A system and a method of the interaction and preservation of two or more reagents used in a chemical reaction is described, in which the reagents are put in contact one with another only when a buffer (A) carrying a sample to be treated with said reagents breaks a partition barrier (4, 14) placed between two containers belonging to a device comprising a first upper container (2, 12) and a second lower container (3, 13) of a test tube (1), the bottom wall of the first container (2, 12) forming said partition barrier (4, 14) able to be perforated by the buffer (A) carrying the sample to be treated.

11 Claims, 5 Drawing Sheets

METHOD AND DEVICE OF RAPID ANTIGEN EXTRACTION

CROSS REFERENCE TO RELATED APPLICATION

This is a continuation-in-part of U.S. application Ser. No. 11/312,167, filed Dec. 20, 2005, now abandoned.

FIELD OF THE INVENTION

The present invention is about a method and a device for preserving two or more reagents used in a chemical reaction as well as for a rapid antigen extraction.

BACKGROUND OF THE INVENTION

Different methods for preserving two or more reagents, in order to put them in contact only when they have to be used for a rapid antigen extraction, are known in the state of the art. For example, in pharmaceutical preparations, a reagent is commonly preserved in a solid state and it is dissolved in a liquid state solvent just before the use, by perforating a mechanical partition wall.

Other preservation methods have been described as well, in which two or more containers, each containing a reagent, are inserted into a single main container inside which, after the breakage of the internal containers, the reagent mixing takes place.

The traditional methods of extraction of saccharidic antigens of group A streptococcus provide for the use of liquid reagents (Lenneft, E. H., Ed., Manual of Clinical Microbiology, Fourth Edition, American Society of Microbiology, Washington, D.C., 1985, pages 170-171). Typically, two liquid reagents are used in the extraction stage: an acid (acetic, hydrochloric or citric acid) and a sodium nitrite solution. The two reagents are mixed in a test tube in which the wad used to take the biological sample to be examined is inserted.

In other known methods, at least one of the two reagents is in a solid state (U.S. Pat. No. 5,536,646), or the reagents are contained in test tubes or flasks with several separate compartments, each containing a single reagents to be mixed immediately before use (U.S. Pat. No. 4,673,639).

By mixing the two reagents, nitrous acid, which is a relatively unstable acid, is produced, thus requiring that the reagents are mixed immediately before the extraction process starts. Otherwise, the instability of the resulting nitrous acid solution can reduce the extraction effectiveness. In fact, if the reagents are prematurely mixed with respect to the biological sample addition, according to what described in U.S. Pat. No. 4,851,337, the nitrous acid decomposition takes place and the extraction solution can lose its effectiveness in a very short time.

According to the method described in U.S. Pat. No. 5,415,994, the extraction takes place in a well directly obtained in the cartridge containing the immunochromatographic strip. One of the two reagents is contained in a flask, that contains on its turn a phial with the second reagent. The operator mixes the two reagents by breaking the phial and then pours the mixture in the well in which the wad is placed. In this way, the operator does not have to count the drop number of each reagent. However, in this case too the extraction takes place after the two reagents have been mixed. Moreover, the insertion of the wad in the well sometimes causes the even partial occlusion of the liquid drainage conduit and thus the flow is slowed down or even blocked. Otherwise, if the wad is inserted in a manner such that the liquid does not flow therethrough before reaching the immunochromatographic chamber, the reaction liquid can reach the immunochromatographic membrane before the extraction takes place.

According to other known methods (U.S. Pat. No. 5,494,801), a third reagent is added to the two default ones in order to neutralize the solution before the chromatographic stage takes place. At present however the use of three reagents is considered too complicated for the operator, and thus the systems providing for the use of two reagents only are preferred. Furthermore, even these methods do not avoid the risk of effectiveness reduction of the extraction due to the time elapsed between the reagent mixing and the sample insertion.

Methods that provide for the insertion of the sample, on which the extraction has to be performed, in a device before adding the reagents have been described too (U.S. Pat. No. 6,168,956). In these methods, the operator must apply the reagents according to the optimal time sequence. However, the need to determine the volume of the reagents (for example, by counting the reagent drops) still remains, as well as the possibility to use the same reagents twice.

The traditional methods of extraction of lipopolysaccharidic antigens from Chlamydia trachomatis provide for the use of an alkaline reagent able to extract the lipopolysaccharidic antigens, in which an acid or a buffer is inserted to neutralise the extraction. According to a traditional method, the alkaline reagent consists of sodium hydroxide and the aid reagent for neutralizing the extraction solution is hydrochloric acid.

The wad through which the biological sample has been taken is inserted into a test tube containing the alkaline reagent for the extraction and it is agitated for a predetermined time, after which the neutralization reagent is added.

SUMMARY OF THE INVENTION

It is thus an object of the present invention to overcome the problems of the aforementioned prior art method and devices.

The present invention can be applied in all the situations in which two or more reagents, that can start a chemical reaction together with a sample to be treated, can not be mixed together before adding the sample. For example, it is possible that the sample has to be put in contact with an unstable reaction product, or with more than one reagent, in a predetermined sequence.

More specifically, the present invention can be applied to the bacterial antigens extraction processes performed with wad in human or animal samples. In particular, the present invention can be used for the extraction of saccharidic antigens from group A and B streptococcus, as well as of lipopolysaccharidic antigens from Chlamydia.

The main object of the method and the device of rapid antigen extraction according to the present invention is thus to simplify the aforementioned prior art extraction processes, in particular:

a) the operator does not have to predetermine and check the reagent volume, for example by counting the dispensed reagent drops;

b) the time needed to dissolve one or more solid state reagents is not required;

c) the time elapsed between the reagent mixing and the insertion of the wad with the biological sample does not reduce the extraction effectiveness, for example when the highly unstable nitrous acid is used.

More in particular, the present invention relates to a method and a device for a diagnostic test employing an immunochromatographic strip, wherein the said strip is dipped in the vial containing the antigen extracted by the reagents provided for in the device's compartments according to the present invention.

BRIEF DESCRIPTION OF THE DRAWINGS

Further characteristics and advantages of the method of rapid antigen extraction according to the present invention, and the device for performing said method, will be better highlighted in the following description of preferred embodiments, given in the explanatory but not limiting way with reference to the annexed figures of drawings, in which.

DESCRIPTION OF THE PREFERRED EMBODIMENTS

Figure 1:
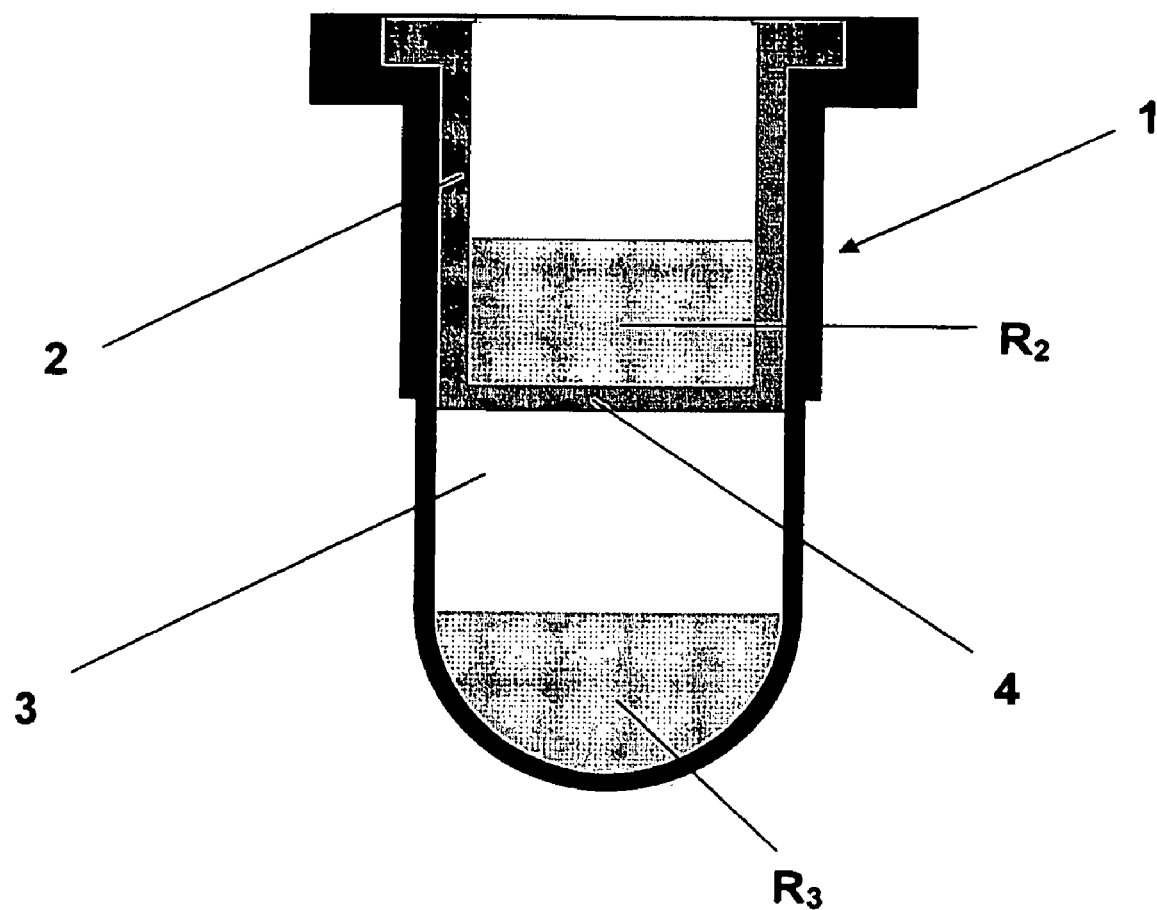
FIG. 1 is a schematic sectional view of a first embodiment of a device for performing the method of rapid antigen extraction according to the present invention.
Figure 3:
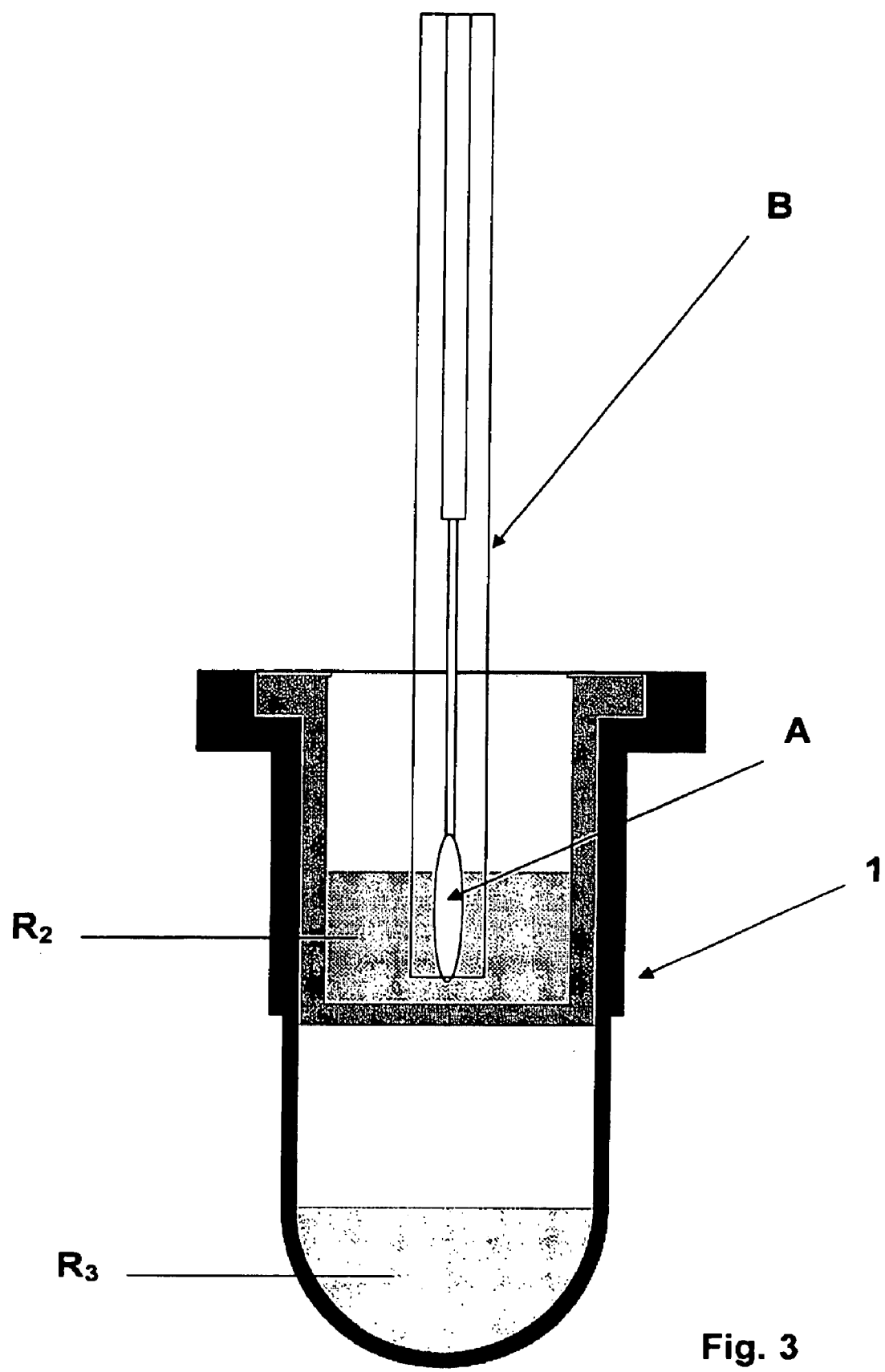
FIG. 3 is a schematic sectional view of an embodiment of a flexible extraction device inserted in a rigid tube for the breakage of the mechanical barrier between the two reagents.

With reference to FIG. 1, according to the method of the invention, the two reagents are poured in predetermined volumes in a preferably but not necessarily cylindrical test tube 1 during the manufacturing stage of the device for performing said method, said test tube 1 comprising a first inner container 2 able to be inserted in a second outer container 3 that forms the main body of the test tube 1. The container 2 is configurated to form a cap for the container 3. The two containers 2 and 3 are then assembled so that the wad A (FIG. 3) with the sample to be tested sequentially passes through the reagent $R_2$, placed inside the container 2, and the reagent $R_3$, placed inside the container 3, respectively, by breaking the mechanical barrier 4 that forms the bottom wall of said container 2 and separates said two reagents $R_2$ and $R_3$. The containers 2 and 3 can be manufactured with any kind of material compatible with the reagents $R_2$ and $R_3$ contained therein, and can have a proper shape and a sufficient volume to contain the wad A, said reagents $R_2$ and $R_3$ being in turn either in liquid or in solid state. The test tube 1 is sealed at its top using any known sealing system, for example with a metallic sheet (not shown).

Figure 2:
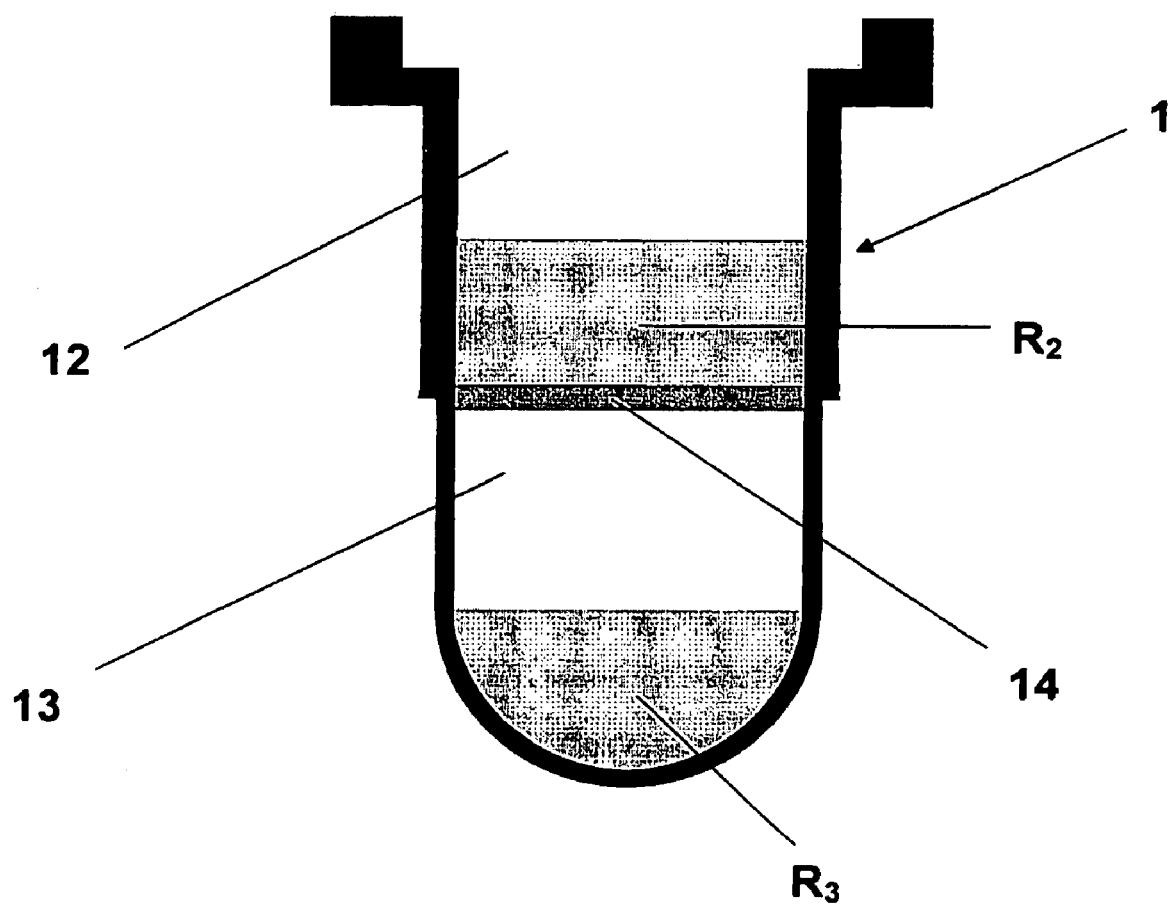
FIG. 2 is a schematic sectional view of a second embodiment of a device for performing the method of rapid antigen extraction according to the present invention.

Another embodiment of the device for performing the method according to the present invention is shown in FIG. 2. After pouring the reagent $R_3$ in the test tube 1, it is possible to form a partition wall 14 in said test tube 1 having the same function of the container 2 mechanical barrier 4, for example by adding solid paraffin, heating it up to its melting and thus letting it cool down until it forms a proper physical partition element 14 similar to said mechanical barrier 4, thus being able to define two separate containers, an upper one 12 and a lower one 13, inside the same test tube 1. At this point it is possible to add the second reagent $R_2$ into the so formed upper container 12 of the test tube 1. In this case too the test tube 1 is subsequently sealed at its top using a known sealing system.

The device consisting of the test tube 1 for performing the method according to the invention is then able to ensure that the two reagents $R_2$ and $R_3$ are put in contact only when the wad A bearing the sample is present. Therefore, according to the method of the invention, the transportation of the first reagent to the second reagent is performed by the wad A itself.

Figure 4:
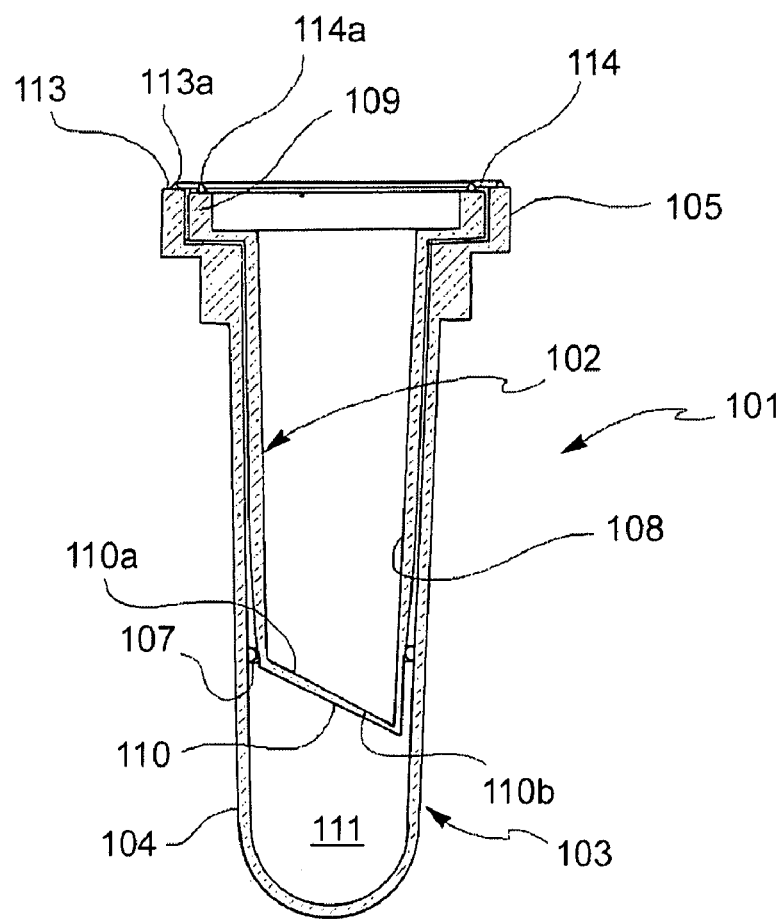
FIG. 4 is a schematic sectional view of a further embodiment of the device of the present invention.
Figure 5:
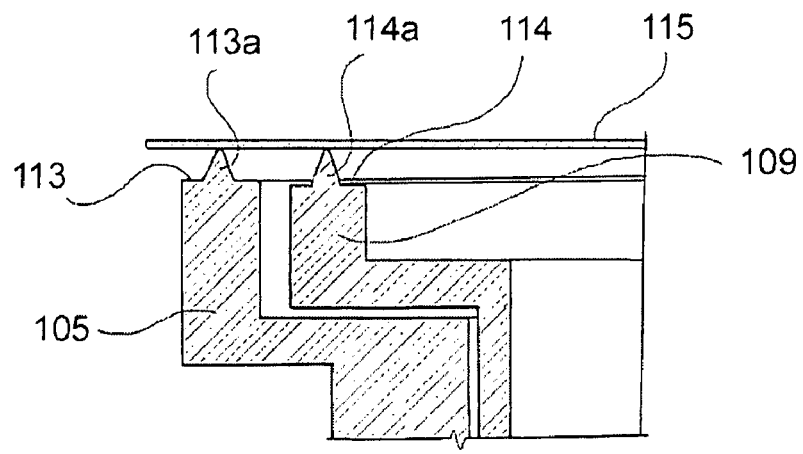
FIG. 5 is a schematic sectional view of a particular of the device of FIG. 4.

Another most preferred embodiment of the invention is shown in FIGS. 4 and 5. A test tube 101 comprises an inner container 102 shaped and configurated to be inserted in an outer container 103 and to form a cap for this latter.

To this end, the outer container 103 comprises a body 104 and an open portion 105. The body 104 is substantially cylindrical in shape and is closed at the bottom, preferably with a rounded profile. Advantageously, the body 104 is tapered downwardly.

The inner surface of the body 104 comprises an annular rib 107 that is situated in a position wherein it can interfere with the outer surface of the inner container 102, while this latter is fitted in the outer container 103, and thus can act as a gasket ring.

The open portion 105 has a larger diameter than the body 104 and presents a stepped internal profile.

The inner container 102 comprises a body 108 and an open portion 109, both having a diameter substantially equal to or slightly less than the internal diameter of the corresponding parts of the outer container 103, so that the inner container 102 can be inserted in the outer container 103 without substantial clearance between the two surfaces. To this end, the body 108 of the inner container 102 is substantially cylindrical in shape and slightly tapered downwardly, in order to follow the profile of the outer container 103.

The body 108 has a closed beveled bottom, so that a proximal connecting portion 110a and a distal connecting portion 110b, with respect to the open portion 109, are defined. The closure wall 110 is substantially planar and has a thickness that decreases from the proximal connecting portion 110a to the distal connecting portion 110b to the body 108. This feature is very important while the wad is inserted in the inner container 102 and, after having absorbed the reagent contained therein, is then forced against the closure wall 110 in order to puncture it. In fact, the beveled shape of the bottom of the inner container 102 together with the smaller thickness of the distal connecting portion 110b allow to concentrate the force in that point and to make easier the puncturing of the wall. Thus, thanks to this particular shape of the closure wall 110, the inner container 102 is made of one piece, so that the barrier to be punctured by the wad can be made of a material, such as polyethylene, that is thicker and more resistant that a paraffin film. This provides for enhanced impermeability and tightness to leakage with respect to the paraffin barriers as normally used in the prior art devices, wherein the paraffin (or similar weak materials) is employed to improve the puncturing action.

Figure 6:
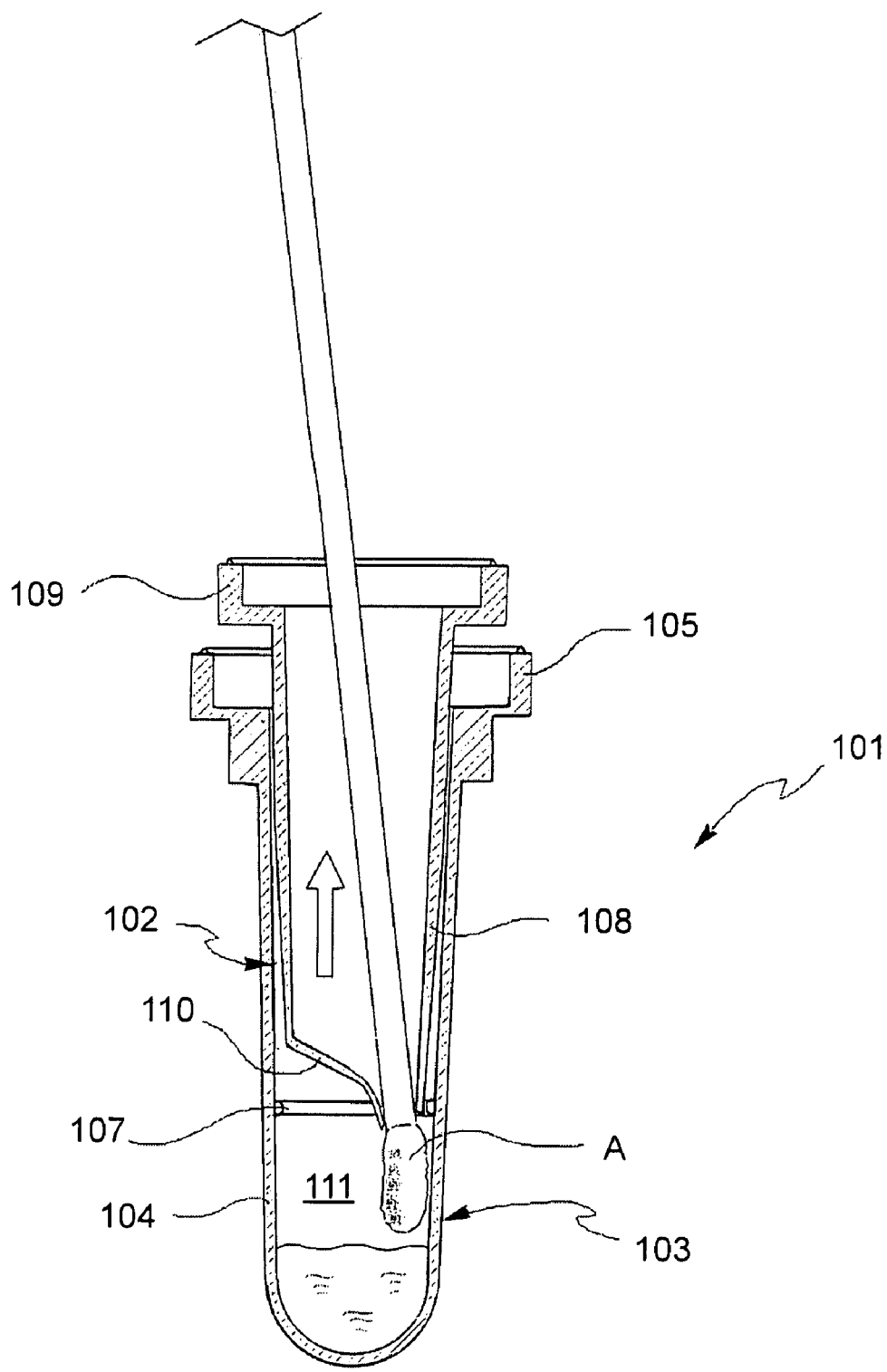
FIG. 6 is a schematic view of the device of FIG. 4 during use.

Another advantage deriving from the use of a harder, thicker material for the closure wall 110 of the inner container 102 is that, when the wad has punctured it and is then removed, it sticks against the stiff edge of the closure wall 110. In such a way, as shown in FIG. 6, the removing action of the wad also brings the inner container 102 out, thus leaving the outer container 103 ready for the subsequent analysis.

The body 108 of the inner container 102 extends for a length that is less than the length of the outer container 103, in order to create in this latter a bottom chamber 111, wherein a reagent $R_3$ can be kept. The length of the inner container 102 is such as to allow the annular rib 107 of the outer container 103 to interfere with the surface of the substantially cylindrical portion of the body 108 above the bottom portion thereof.

The open portion 109 of the inner container 102 has an external profile that can substantially fit with the internal profile of the corresponding portion of the outer container 103. To this end, the outer surface of the open portion 109 of the inner container 102 is stepped.

In a particularly preferred embodiment of the invention, the upper rims 113, 114 of the outer and inner containers 103, 102, respectively, have tooth-shaped annular corrugations 113a, 114a. As shown in FIG. 5, these corrugations 113a, 114a serve the function of allowing a secure welding of a closure sheet 115, such as a conventional peelable metallic sheet. In fact, in absence of such corrugations, it may happen that the upper rims 113, 114 of the inner and outer containers 102, 103 are not perfectly levelled, so that the closure sheet can be welded on one rim only. As a consequence, leakage can occur or the internal reagents can be contaminated by outside.

Conversely, the tooth-shaped corrugations 113a, 114a are sufficiently thin to melt during the thermal welding of the closure sheet 115, so that they auto-level themselves to give a complete and efficient welding.

Very preferably, the outer container 103 is made of a flexible material, such as polyethylene. This allows the body 104 to be squeezed when the wad, after having put into contact, the two reagents $R_2$ and $R_3$, is removed from the test tube 101, thus assuring that the whole antigen solution is released from the wad.

Preferably, both the inner container 102 and the outer container 103 are made of the same material such as polyethylene.

As in the previous embodiments, in this case too the two reagents $R_2$ and $R_3$ are poured in predetermined amounts in the inner and in the outer containers 102, 103, respectively, during the manufacturing stage of the device, which is then sealed on the top openings with conventional peelable films.

During use of the device, the sealing film is removed and the wad—which was previously used to contact a body fluid or mucuous membrane of a patient—is dipped in the inner container 102 in order to contact the reagent $R_2$ contained therein. After the required time is elapsed, the wad is pushed to puncture the closure wall 110 of the inner container 102 and is then put into contact with the reagent $R_3$. At this time the reaction takes place and the extraction of the antigen from the wad is performed. After the prescribed time is elapsed, the wad is removed by simultaneously squeezing the body 104 of the outer container 103 in order to squeeze also the wad to release all the antigen solution imbibed thereon. After squeezing the wad, the removal of the wad is completed and this action allows the inner container 102 to be removed together with the wad, as explained above. At this stage, the outer container 103, containing the whole antigen solution to be tested, is ready for the subsequent analysis. The analysis is typically an immunochromatographic test performed by means of a strip that is dipped in the antigen solution directly in the outer container 103 of the test tube 101. In this connection, the fact that the removal of the inner container 102 does not leave any residue of the barrier separating the two containers in the outer container 103 (as this barrier is associated with the removed inner container 102), avoids the risk that the strip test is altered by the presence of solid material that could interfere with the capillarity movement of the liquid solution on the strip.

According to a preferred aspect of the invention, the sample is taken with a pharyngeal wad A following well known procedure. The wad A is then inserted into the first container 2 or 12 of the test tube 1, after the removal of the seal, and it is then driven in the second container 3 or 13, by breaking the barrier 4 between the containers 2 and 3 or the partition wall 14 between the containers 12 and 13. The extraction of the antigen by means of the so formed nitrous acid is thus started. When the expected extraction time is lapsed, the wad A is removed, preferably with the first container 2 if present, from the test tube 1 and the liquid can be poured directly from said test tube 1 into the immunochromatographic device for the antigen detection.

For example, according to the method of the invention, the reagent $R_2$ contained in the first container 2, 12 can be a 0.4 M acetic acid. The operator inserts the wad A into the first container 2, 12 of the test tube 1. The reagent $R_2$ is almost fully absorbed by the wad A. By pushing the wad A against the bottom 4, 14 of the container 2, 12, said bottom 4, 14 breaks, allowing said wad A to pass through and thus to reach the reagent $R_3$, for instance a 2 M sodium nitrite, in the second container 3, 13. At this point, the nitrous acid formation reaction takes place. Therefore, if the antigen is present, the antigen extraction takes place in the best conditions for the effectiveness of said extraction. Once the expected time for the extraction of the bacterial antigens from the wad A is lapsed, the wad A is removed from the test tube 1 and the liquid can be poured in the immunochromatographic strip cartridge well.

Another example of the method according to the present invention allows to extract Chlamydia antigens from cervical or urethral wads. The sample is taken with a cervical or urethral wad according to well known procedures. The wad is then inserted into the first container 2, 12 of the test tube 1, after the removal of the said test tube seal, and it is left in contact with the reagent $R_2$ for the required extraction time. Once the extraction is finished, the wad is pushed into the second container 3 by breaking the barrier 4, or into the second container 13 by breaking the partition wall 14, and it is put in contact with the neutralization reagent $R_3$.

In this case, the reagents comprise an alkaline reagent ($R_2$) and an acidic neutralization reagent ($R_3$).

According to a traditional method, the cervical o urethral wad is inserted into a test tube containing 5 drops of 0.2 N sodium hydroxide, and it is left in the solution for 2 minutes. After shaking the wad, a predetermined volume of 0.1 N hydrochloric acid is added to neutralize the extraction solution. After shaking the wad again, said wad is then removed and a certain volume of the extraction solution is added to the test cartridge.

In order to take biological samples from particular sites, for example from the nasal cavities or the urethra, devices having a flexible and thin structure are available on the market, thus being difficult to break the partition wall between the two reagents with said devices. In this case, the sampling device can be inserted in advance into an assembly provided with the proper stiffness and resistance features for breaking the partition wall. For example, after the insertion of the sampling wad A into the test tube 1, 101, it is possible to surround said wad A with a tube B having a proper diameter. By pushing the tube B, that breaks the barrier 4 or the closure wall 110, the wad A is transported into the container 3, 13, 103 (see FIG. 3).

It should be understood that several modifications could be made to the device, formed by the test tube 1, 101, that performs the method of rapid antigen extraction according to the present invention, as it is also defined in the appended claims. For example, the sealing of the test tube 1 can be obtained by using a cap, or by thermal sealing with an aluminum sheet coupled with polyethylene. Furthermore, although in the description the sample collection system is indicated as a "wad", this denomination is merely used for convenience, since the most common systems for taking the A group streptococcus are the pharyngeal wads, while the most common systems for taking the Chlamydia trachomatis are the cervical or urethral wads. Therefore, it should be obvious for a man skilled in the art that it is possible to use any sampling system compatible with the immunological array format.

I claim:

1. A test tube for performing antigen extraction from a wad, the said device comprising a test tube which comprises an inner container and an outer container, the inner container being shaped and configured to be inserted in said outer container and to form a closure cap for this outer container, a bottom chamber delimited between a bottom of said inner container and a bottom of said outer container, at least the said outer container being made of a flexible material that allows it to be squeezed between the fingers of an operator.

2. The test tube of claim 1, wherein the outer container comprises a body and an open portion, the body having cylindrical walls which are tapered downwardly.

3. The test tube of claim 1, wherein the inner surface of the body of said outer container comprises a gasket ring provided by an annular rib that is situated to delimit a top of said bottom chamber, in a position wherein it can interfere with the outer surface of the inner container, while this latter is fitted in the outer container.

4. The test tube of claim 1, wherein the said inner container comprises a body and an open portion, both having a diameter substantially equal to or slightly less than the internal diameter of the corresponding body and open portion of the outer container, so that the inner container can be inserted in the outer container without substantial radial clearance therefrom.

5. The test tube of claim 4, wherein the said body of the inner container has a closed beveled bottom having a closure wall wherein a proximal connecting portion and a distal connecting portion, with respect to the said open portion, are defined, wherein the said closure wall has a thickness that decreases from the said proximal connecting portion to the said distal connecting portion.

6. The test tube of claim 4, wherein the said body of the inner container extends for a length that is less than the length of the outer container, in order to create said bottom chamber, wherein a reagent ($R_3$) can be kept, the length of the said body of the inner container being such as to allow the annular rib of the outer container to interfere with the surface of the substantially cylindrical portion of the said body above the bottom portion thereof.

7. The test tube of claim 1, wherein the upper rims of the outer and inner containers, respectively, have tooth-shaped annular corrugations welded to a closure sheet.

8. The test tube of claim 1, wherein the said inner container is made of one piece.

9. The test tube of claim 1, wherein said inner and outer containers are made of polyethylene.

10. A method of extracting an antigen from a wad wherein the said antigen is absorbed or adsorbed, comprising the following steps:

providing a device according to claim 1, wherein a first reagent ($R_2$) is contained in said inner container and a second reagent ($R_3$) is contained in said outer container;

dipping the said wad in the inner container in order to contact the said reagent ($R_2$) contained therein;

after a predetermined time is elapsed, pushing the said wad to puncture the bottom wall of the inner container and putting the said wad into contact with the second reagent ($R_3$) in the said outer container;

after a prescribed time is elapsed, removing the said wad by simultaneously squeezing the body of the outer container in order to squeeze also the wad to release all the antigen solution imbibed thereon;

completing the removal of the wad, wherein the said wad interferes with the inner container in order to remove the said inner container simultaneously with the wad.

11. The method of claim 10, further comprising the step of dipping an immunochromatographic strip in the antigen solution directly in the said outer container of the test tube.

\* \* \* \* \*